United States Patent
Hafer et al.

(10) Patent No.: US 7,352,960 B2
(45) Date of Patent: Apr. 1, 2008

(54) MODIFIED AIR FRESHENER DEVICE

(75) Inventors: Kevin Hafer, Phoenix, AZ (US); Rick Althouse, Scottsdale, AZ (US)

(73) Assignee: The Dial Corporation, Scottsdale, AZ (US)

( * ) Notice: Subject to any disclaimer, the term of this patent is extended or adjusted under 35 U.S.C. 154(b) by 95 days.

(21) Appl. No.: 11/405,193

(22) Filed: Apr. 17, 2006

(65) Prior Publication Data

US 2006/0291826 A1 Dec. 28, 2006

Related U.S. Application Data

(60) Provisional application No. 60/672,641, filed on Apr. 18, 2005.

(51) Int. Cl.
*F24F 6/08* (2006.01)
*F24F 6/00* (2006.01)

(52) U.S. Cl. .................... 392/395; 392/392

(58) Field of Classification Search ......... 392/386–406
See application file for complete search history.

(56) References Cited

U.S. PATENT DOCUMENTS

| | | | |
|---|---|---|---|
| 5,290,546 A | 3/1994 | Hasegawa et al. | |
| 6,104,867 A | 8/2000 | Stathakis et al. | |
| 6,594,445 B2 | 7/2003 | Millan | |
| 6,661,967 B2 | 12/2003 | Levine et al. | |
| 6,697,571 B2 | 2/2004 | Triplett et al. | |
| 6,766,773 B2 | 7/2004 | Wolpert et al. | |
| 6,768,865 B2 | 7/2004 | Stathakis et al. | |
| D508,558 S | 8/2005 | Wolpert et al. | |
| 7,082,259 B2 * | 7/2006 | Zobele | 392/390 |

* cited by examiner

*Primary Examiner*—Sang Paik
(74) *Attorney, Agent, or Firm*—Frank T. Barber

(57) ABSTRACT

A heating device for the vaporization of active substances, such as air freshener fragrances, disinfectants, sanitizing agents, insecticides and the like, in which a wick is immersed in a fluid active substance and heat is applied to produce vaporization. The heating is produced by one or more electrical resistance elements embedded in a circular heating ring which is hinged to move over the end of the wick and encircle it. The internal wires which carry electrical current from a source of electrical power are led through the hinged area for connection to the electrical resistance elements, and a feature of the invention is the protection of such wires as they pass through the hinged area.

6 Claims, 2 Drawing Sheets

MODIFIED AIR FRESHENER DEVICE

CROSS REFERENCE TO RELATED APPLICATION

This application claims priority to U.S. Provisional Patent Application Ser. No. 60/672,641, entitled "Modified Air Freshener Device", filed on Apr. 18, 2005.

FIELD OF THE INVENTION

This invention relates to vapor-dispensing devices, and more particularly to management of the electrical wiring utilized in the heating unit for promoting vaporization of the volatile materials used in said devices.

BACKGROUND OF THE INVENTION

Electrical liquid vaporizers (often referred to as "liquid electrics") are generally well known in the prior art. The primary function of these types of devices has generally been the counteracting of malodors through the delivery of aesthetically pleasing fragrance vapors, or facilitating the delivery of other vapors, such as insecticides or other compositions.

Typically, such electric liquid vaporizers comprise a housing unit configured to receive a bottle or liquid container portion. The bottle portion contains a wick or wicking system through which the volatile liquids can be migrated to a portion of the wick that is exposed to the air. The exposed portion of the wick is generally heated by a heating element disposed within the housing unit and proximate to the wick in order to suitably facilitate the vaporization of the volatile liquid to be dispensed therefrom. In vaporizers adapted to accommodate refill bottles when the contents of the bottle have been consumed, the bottles may be releasably attached to the housing. For example, the neck of the bottle may be threaded and engaged within the housing unit in a screw-like manner, or the bottle may be interconnected to the housing unit in a "snap-and-fit" manner.

In devices of this nature, the heating element delivers kinetic energy to molecules of the liquid as contained in the wick, thereby increasing the rate of evaporation to obtain higher fragrance intensity and uniform delivery density over time. Typically, in such units, the back side of the housing is equipped with electrical prongs that may be plugged into a conventional electrical outlet, and lead wires connected to such prongs are run through the body of the unit to the resistance elements in the heater located in the vicinity of the upper end of the wick, thereby causing the heating unit to heat the liquid and vaporized liquid that have been drawn up into the wick. Depending on the configuration and the aesthetic design of the vaporizer unit, the distance traveled by these lead wires may be considerable, and care must be used to keep them separated along the path of their travel.

In the vaporizer unit utilized in the present invention, an elongated plastic wire guidance frame is used for protecting and guiding these lead wires. Such frame is positioned on the interior of the housing with its bottom end located adjacent the electric prongs, and it extends upwardly, parallel to the longitudinal axis of the wick, to terminate at its upper end in a circular ring structure in which the electrical resistance elements are embedded. The main body of the plastic frame is connected to said circular ring structure by a hinge, and in assembly the ring structure is bent over to a 90° angle to encircle the upper portion of the wick. The lead wires from the electric resistance elements embedded in the circular ring structure are guided through the hinged area downwardly along the body of the plastic frame to the point where they are connected to the electric prongs. A feature of the present invention is the protection of such lead wires in this special environment.

SUMMARY OF THE INVENTION

The present invention provides a vaporizing device including a system of guidance and protection for the electric warmer lead wires in the course of their run from the electric prongs at one end of the vaporizing device to their connection with the resistance element or elements in the electric warmer that is used to heat and facilitate the liquid and liquid vapor that has been drawn up into the wick. The invention has particular applicability to the protection and guidance of the said lead wires to prevent them from touching as they pass through the hinged area of the wire guidance frame.

In accordance with one exemplary embodiment of the present invention, the warming device may include a plastic housing having a front side and a back side and an open bottom for receiving a refill bottle; a refill bottle unit containing an active liquid material and including a wick in fluid communication with said active material, said refill bottle being positioned in said housing with said wick extending out the top of said bottle and upwardly in said housing; an elongate longitudinally extending plastic frame, positioned in said housing in proximity to said bottle and wick, with its longitudinal axis parallel to the longitudinal axis of said wick; a circular heating ring hingedly connected to the upper end of said plastic frame and configured to be bent over the top of and to encircle said wick; at least one electric resistance element being positioned on the interior of said circular heating ring; said resistance element being fitted with a pair of resistance wire leads; said longitudinally extending frame having at least one longitudinally extending rib for providing at least a pair of longitudinal channels, and being fitted at its lower end with a pair of electrical prongs in a plug unit for use in an electrical outlet; said electrical prongs in said plug unit extending outwardly through the back side of said housing; said pair of electrical resistance wire leads extending from said resistance element, each wire being positioned in a separate one of said channels and being connected to respective prongs in said plug unit; and at least one projection on the body of said circular heating ring adjacent the said hinge, to guide the respective resistance wire leads through the hinge area and into separate longitudinal channels.

BRIEF DESCRIPTION OF THE FIGURES

Additional aspects of the present invention will become evident upon reviewing the non-limiting embodiments described in the specification and the claims taken in conjunction with the accompanying figures, wherein like numerals designate like elements:

DETAILED DESCRIPTION OF EXEMPLARY EMBODIMENTS

The following description is of exemplary embodiments of the invention only, and is not intended to limit the scope, applicability or configuration of the invention in any way. Rather, the following description is intended to provide a convenient illustration for implementing various embodiments of the invention. As will become apparent, various changes may be made in the function and arrangement of the elements described in these embodiments without departing from the scope of the invention as set forth in the appended claims.

Figure 1:
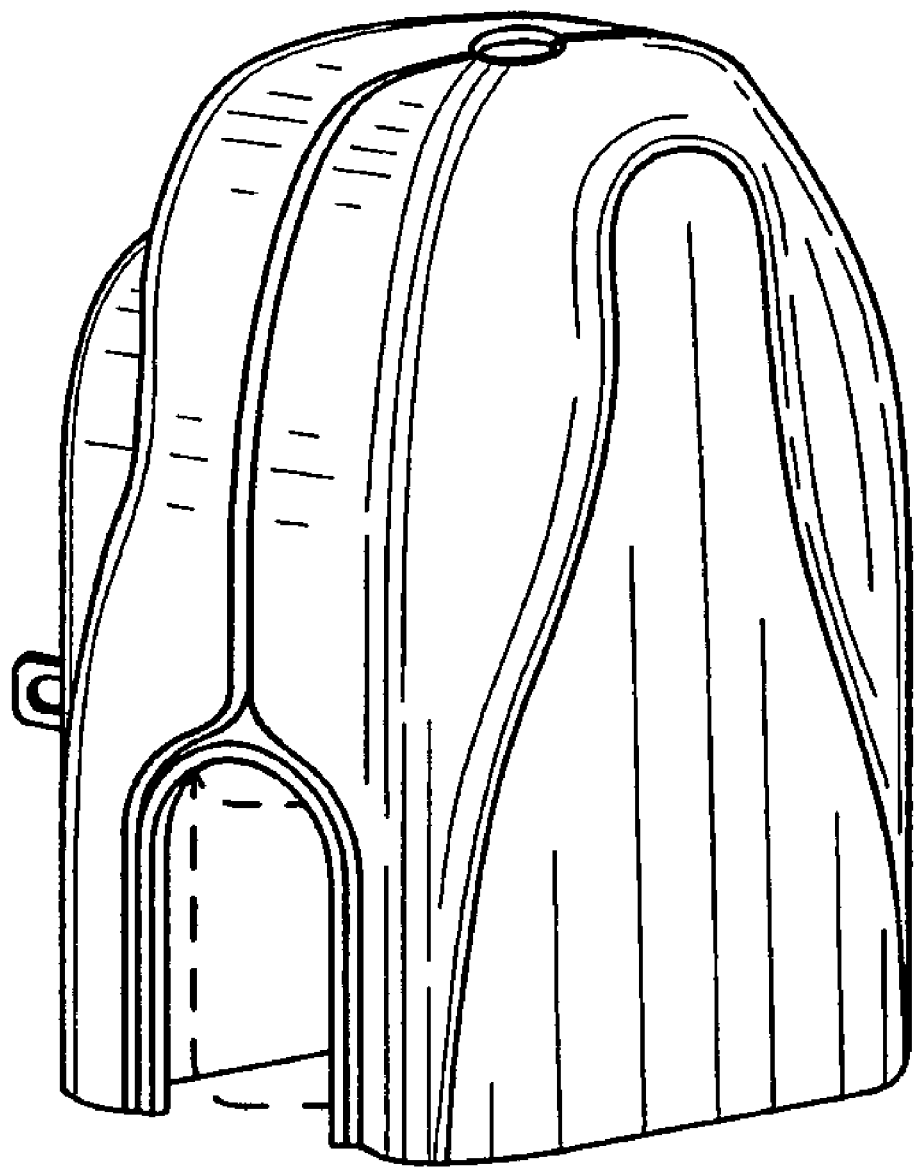
FIG. 1 is a perspective overall view showing the front and side of the outside of one embodiment of the heating device of the present invention.

In one exemplary embodiment of the invention, a vaporizing device, as shown in FIG. 1, may comprise a housing 10, a refill bottle or reservoir 12, and an electric plug 14 at the back side of the housing for plugging into a conventional electrical outlet in order to obtain electrical current for heating the contents of the refill bottle and thus facilitating the dispensing of vapors into the surrounding atmosphere.

Figure 2:
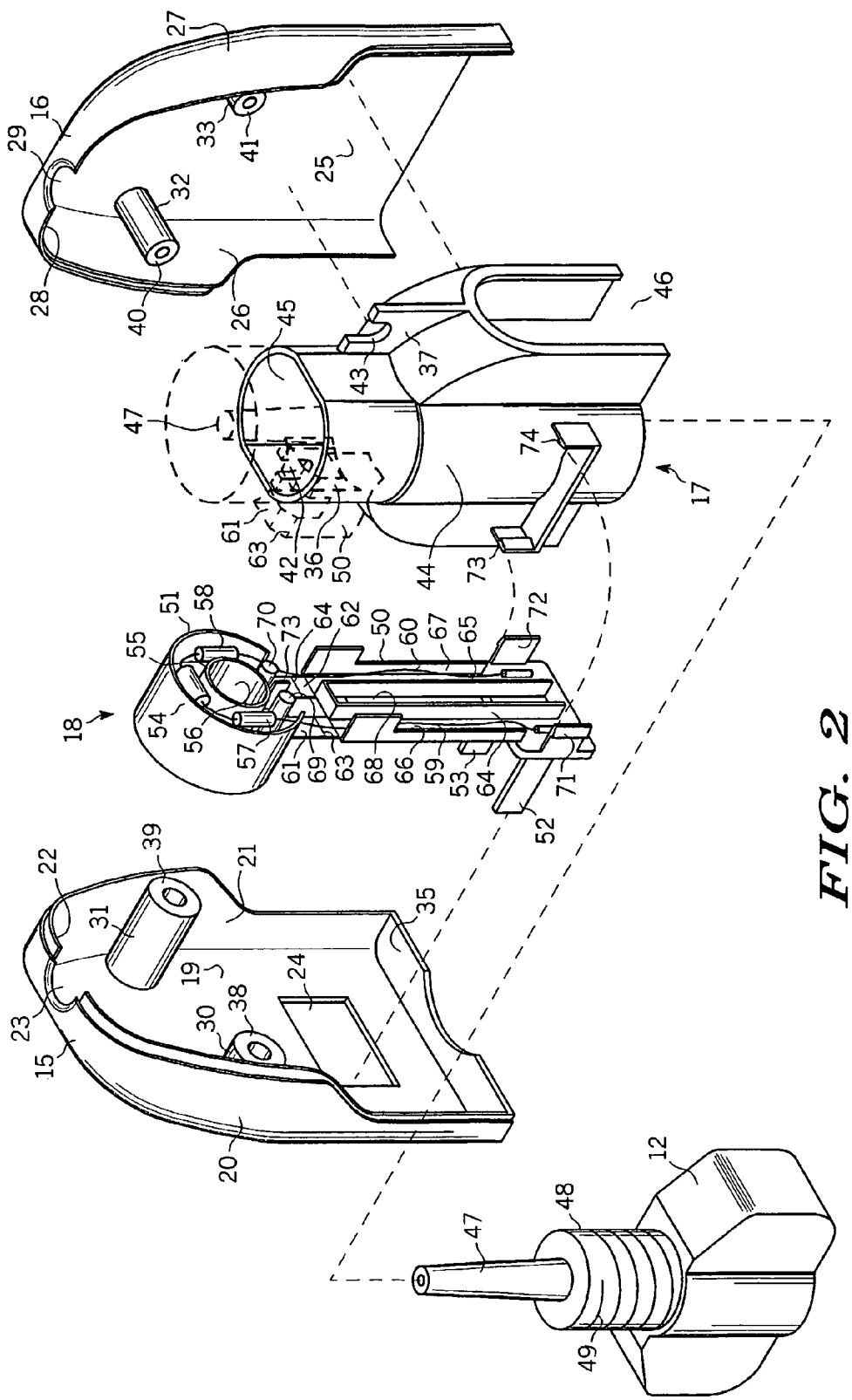
FIG. 2 is an exploded view of the interior of an embodiment of a heating device, showing the front and back sides of the housing, the elongate wire guidance frame, the interior bottle holding support, and the refill bottle, in accordance with the present invention.

As shown in FIG. 2, the housing 10 comprises a back cover 15 and a front cover 16, and two major interior components—namely, a bottle holder 17 and an elongate wire guidance frame 18. FIG. 2 also shows the refill bottle 12 which may be inserted in the interior of the housing, and subsequently removed for replacement.

The back cover 15 has a generally flat back side 19, and side panels 20 and 21, which curve around to form a top panel 22, having a vent opening 23. In the lower part of the back side 19, an aperture 24 is provided for allowing the electric plug 14 to extend through the back side for plugging into an electrical outlet. The front cover 16 has a generally flat front side 25, and side panels 26 and 27, which curve around to form a top panel 28, having a vent opening 29. When the bottle holder 17 and the elongate wire guidance frame 18 are assembled (as will be described hereinafter) and positioned on the back cover 15, the device may be closed by placing the front cover 16 over the back cover 15 so that the edges of side panels 20 and 21 and top panel 22 of the back cover 15 mate with the edges of the side panels 26 and 27 and the top panel 28 of the front cover 16. The device is secured in this closed position by use of screws applied through the pair of screw posts 30 and 31 in the back cover, which mate with the pair of screw posts 32 and 33 in the front cover. In the closed position, the semicircular vent opening 23 in the back cover mates with the semicircular vent opening 29 in the front cover, to provide a full vent for outward passage of vaporized material. The various parts of the housing may be formed from suitable materials, including plastics such as polypropylene or high density polyethylene.

The bottle holder 17 is an interior component in the housing and is designed to serve a dual function—namely, a structure for holding the refill bottle 12 and also for anchoring the elongate wire guidance frame 18. When the bottle holder 17 and the elongate wire guidance frame 18 are assembled (as will be described hereinafter), the assembly may be secured to the back cover 15 by placing the bottom edge 34 of the bottle holder 17 on the bottom shelf 35 of the back cover and is secured in place there by a peg and hole arrangement (not shown). Following this, the two positioning tabs 36 and 37 on the bottle holder 17 are placed on the top surfaces 38 and 39 of screw posts 30 and 31, respectively, of the back cover 15, and the device may then be closed by placing the front cover 16 over the back cover 15 so that the edges of side panels 20 and 21 and top panel 22 of the back cover 15 mate with the edges of the side panels 26 and 27 and the top panel 28 of the front cover 16. As previously mentioned, the device is secured in this closed position by use of screws applied through the pair of screw posts 30 and 31 in the back cover, which mate with the pair of screw posts 32 and 33 in the front cover. In this position, the top portion of the positioning tabs 36 and 37 of the bottle holder 17 are held between the top surfaces 38 and 39 of the screw posts 30 and 31 on back cover 15 and the top surfaces 32 and 33 of screw posts 32 and 33 on front cover 16. The top areas of positioning tabs 36 and 37 are provided with notches 42 and 43 to enable through passage of the securing screws.

As will be seen in FIG. 2, the bottle holder 17 has a central cylindrical body 44 with an open cylindrical top 45. The bottle holder 17 also has an open bottom 46, enabling the refill bottle 12 with upwardly extending wick 47 to be inserted upwardly into the interior of the housing and held in place by a "snap-and-fit" arrangement. When the refill bottle 12 is fully inserted up into the bottle holder 17, the wick 47 extends upwardly through the open top 45 of the central cylindrical body 44. In FIG. 2, the wick 47 in this fully extended upward position is shown in phantom dotted lines.

Preferably, refill bottle 12 is a conventional bottle or similar device configured to receive a volatilizable material and hold the wick 47 firmly in place. The neck 48 of the bottle 12 may be threaded and thus includes a plurality of threads 49. The threads 49 are suitably configured to receive, for example, a cap securing the refill bottle 12 prior to use. The wick 47 preferably extends to the bottom of the refill bottle 12.

In the present embodiment, refill bottle 12 comprises a plastic material that is compatible with the material to be vaporized. For example, refill bottle 12 may be formed of polypropylene, barex and/or PET. However, in certain applications, it may be desirable for bottle 12 to be formed of other materials such as glass or the like. Preferably, bottle 12 is suitably sized for use in connection with household use. In accordance with various aspects of the invention, bottle 12 is preferably configured for receipt of between 25 to about 75 milliliters of liquid material. The weight and moment of the device of the present invention, inclusive of the refill bottle 12 is such that the center of gravity is appropriately positioned and the weight is less than that which would otherwise cause the device to be stable in the electrical outlet.

Wick 47 may be formed from any conventional wick material. Suitable wick materials include porous/sintered plastics such as high density polyethylene and polypropylene, bonded fibers, glass sintered fibers, ceramic materials, carbon fibers, sintered carbon, wood, compressed wood composites, bundled or woven material fibers, or bundled or manmade fibers. In general, wick 47 may be formed of any suitable material now known or hereafter devised by those skilled in the art.

In accordance with various embodiments of the invention, the vaporizable material contained in the refill bottle 12 may be any number of conventional materials dispensed from vapor dispensers, including fragrances, disinfectants, sanitizing agents, insect repellants, insecticides, and the like.

As shown in FIG. 2, the remaining component on the interior of the housing 10 is the elongate wire guidance frame 18, which is positioned in the housing 10 in proximity to said refill bottle 12 and said wick 47, with its longitudinal axis parallel to the longitudinal axis of the wick 47. In a particular embodiment of the invention, the part 18 is molded from a single piece of plastic and is comprised of two main parts—namely, a lower elongate guidance body 50 and an upper circular heating ring 51. Electrical prongs 52 and 53 are anchored at the bottom end of the guidance body 50, and extend outwardly from the back side of the guidance body 50, for plugging into a conventional electrical outlet. As will be seen in FIG. 2, the heating ring 51 is in the form of a circular trough having concentric outer and inner walls 54 and 55 with an open central passageway 56.

Electrical resistance elements 57 and 58, for producing the heat needed for enhancing the evaporation of vaporizable material from the wick 47, are positioned in opposing locations on the interior of the heating ring 51, and a pair of electrical lead wires 59 and 60 are connected to the resistance elements 57 and 58 and are guided down the length of the guidance body 50 for connection at the other end with the electric prongs 52 and 53. When the prongs 52 and 53 are plugged into an electric wall outlet, the current that runs through the lead wires 59 and 60 causes heating of the resistance elements 57 and 58. The plastic tabs 61 and 62 are transversely scored (see score marks 63 and 64) to enable hinging of the circular heating ring 51 at the score marks, so that, in assembling of the unit, the circular heating ring 51 can be bent to a 90° angle thereby encircling the upper end of the adjacent fragrance-containing wick 47. This positioning of the circular heating ring 51 in a bent position encircling the wick 47 is shown in FIG. 2 in phantom dotted lines at the top of the bottle holder 17, with the bottom surface of the circular heating ring 51 resting on the top edge 63 of the central cylindrical body 44 of the bottle holder 17.

It is a feature of the invention that special means are utilized to protect the lead wires 59 and 60 and prevent them from breaking or contacting each other as they carry the electrical current from the electric prongs 52 and 53 through the various stages until they reach the resistance elements 57 and 58. The lower elongate guidance body 50 is provided with a pair of longitudinal ribs 64 and 65, which produce a pair of channels 66 and 67 with an intermediate buffer space 68 in between. Thus lead wire 59 runs the length of the elongate guidance body 50 while contained in channel 66, and lead wire 60 runs the length of the body 50 while contained in channel 67, all with an effective buffer channel 68 between the two. The hinging and bending, which take place in the hinge area where the plastic tabs 61 and 62 are scored, create special opportunities for the lead wires 59 and 60 to be bent, distorted or broken, and it is a feature of the invention that at least one projection or post is mounted in the hinge area to guide the wires through this area. In the embodiment shown in FIG. 2, this feature comprises a pair of cylindrical pegs or posts 69 and 70. As will be seen, guide post 69 causes the lead wire 59 to be threaded between the post and the outer wall 54 of the circular heating ring 51, and guide post 70 causes the lead wire 60 to be threaded between the post and the outer wall 54, thus keeping the two wires thoroughly isolated as they experience the bending and distortion in the hinge area. Further protection of this nature may be gained by use of a plastic rib 73 separating the guide posts 69 and 70, as shown in FIG. 2.

In assembling the various component parts of the heating device, the elongate longitudinally extending plastic frame 50, with its resistance elements 57 and 58, its electric prongs 52 and 53, and its electric lead wires 59 and 60 installed, is mounted on the bottle holder 17 by snap fitting locking tabs 71 and 72 (near the bottom of frame 50) over locking ribs 73 and 74 (near the bottom of bottle holder 17); pressing frame 50 along its longitudinal length against the longitudinal length of bottle holder 17; and then bending the circular heating ring 51 to a 90° angle so that the heating ring can be pressed into position with the bottom surface of the circular heating ring 51 resting on the top edge 63 of the central cylindrical body 44 of the bottle holder 17, as shown in phantom dotted lines in FIG. 2. This two-component system is then placed in position on the inside of the back cover 15 of the housing, with the electric prongs 52 and 53 extending through the aperture 24 in the back cover 15. The device may then be closed by placing the front cover 16 over the back cover 15 so that the edges of side panels 20 and 21 and top panel 22 of the back cover 15 mate with the edges of the side panels 26 and 27 and the top panel 28 of the front cover 16. As previously mentioned, the device is secured in this closed position by use of screws applied through the pair of screw posts 30 and 31 in the back cover, which mate with the pair of screw posts 32 and 33 in the front cover. As a last step, the refill bottle 12, with its protective cap removed, may then be inserted up into the bottom of the device and snapped into position so that the top part of the wick 47 extends up into the area where it is encircled by the circular heating ring 51, which will heat and cause vaporization of the vaporizable liquids when the device is plugged into a conventional electric wall outlet.

Although the present invention has been disclosed in connection with certain preferred embodiments thereof, variations and modifications may be made by those skilled in the art without departing from the principles of the invention. All of these variations and modifications are considered to be within the true spirit and scope of the present invention as disclosed in the foregoing description and defined by the claims.

We claim:

1. A heating device for the vaporization of active substances, in which a wick that is immersed in a fluid active substance is heated to produce vaporization of the active substance, said heating device comprising:
   a plastic housing having a front side and a back side and an open bottom for receiving a refill bottle,
   a refill bottle unit containing said active substance and including a wick in fluid communication with said active material, said refill bottle being positioned in said housing with said wick extending out the top of said bottle and upwardly in said housing,
   an elongate longitudinally extending plastic frame, positioned in said housing in proximity to said bottle and wick, with its longitudinal axis parallel to the longitudinal axis of said wick,
   a circular heating ring hingedly connected to the upper end of said plastic frame and configured to be bent over the top of and to encircle said wick,
   at least one electric resistance element being positioned on the interior of said circular heating ring, said resistance element being fitted with a pair of resistance wire leads,
   said longitudinally extending frame having at least one longitudinally extending rib for providing at least a pair of longitudinal channels, and being fitted at its lower end with a pair of electrical prongs in a plug unit for use in an electrical outlet,
   said electrical prongs in said plug unit extending outwardly through the back side of said housing,
   said pair of electrical resistance wire leads extending from said resistance element, each wire being positioned in a separate one of said channels and being connected to respective prongs in said plug unit, and
   at least one projection on the body of said circular heating ring adjacent the said hinge, to guide the respective resistance wire leads through the hinge area and into separate longitudinal channels.

2. A heating device in accordance with claim 1, wherein said at least one projection adjacent said hinge is a pair of cylindrical pegs.

3. A heating device in accordance with claim 2, wherein said cylindrical pegs are separated by a plastic rib for assisting in guiding the resistance wires through the hinge area.

4. A heating device in accordance with claim 1, wherein said at least one electric resistance element comprises a pair of resistance elements connected in series and positioned on the interior of said circular heating ring, thus providing for a pair of resistance wire leads to be guided through the said hinge area and through the said channels in said elongate frame for connection to said electrical prongs.

5. A heating device in accordance with claim 1, wherein said elongate plastic frame and said circular heating ring comprise a plastic body molded as a single part having a plastic hinge connecting the said frame and said ring.

6. In a heating device for the vaporization of active substances, in which a wick that is immersed in a fluid active substance is heated to produce vaporization of the active substance, and in which said heating is produced by one or more electrical resistance elements adjacent said wick, and in which the electrical power to said electrical resistance elements is supplied through at least two wires that pass through a hinge area, the improvement comprising one or more guide posts positioned between said wires in the hinge area to guide said wires to keep them separated and protect them against distortion or touching in said area.

* * * * *